United States Patent
Bian et al.

(10) Patent No.: US 9,783,519 B2
(45) Date of Patent: Oct. 10, 2017

(54) PALLADIUM/SILVER CO-CATALYZED TANDEM REACTIONS SYNTHESIS OF PHENYLACETOPHENONE DERIVATIVES BY OXABENZONORBORNADIENES WITH TERMINAL ALKYNES AND THEIR ANTI-TUMOR OR ANTI-CANCER ACTIVITIES

(71) Applicants: Hong Kong Baptist University, Kowloon (HK); Yunnan Minzu University, Kunming, Yunnan (CN)

(72) Inventors: Zhaoxiang Bian, Kowloon (HK); Chengyuan Lin, Kowloon (HK); Huaixue Mu, Kowloon (HK); Baomin Fan, Yunnin (CN); Yongyun Zhou, Yunnin (CN); Jingchao Chen, Yunnan (CN); Aiping Lu, Kowloon (HK); Albert Sun-Chi Chan, Kowloon (HK)

(73) Assignees: HONG KONG BAPTIST UNIVERSITY, Kowloon Tong, Kowloon (HK); YUNNAN MINZU UNIVERSITY, Kunming, Yunnan (CN)

( * ) Notice: Subject to any disclaimer, the term of this patent is extended or adjusted under 35 U.S.C. 154(b) by 0 days.

(21) Appl. No.: 14/743,209

(22) Filed: Jun. 18, 2015

(65) Prior Publication Data
US 2016/0368890 A1 Dec. 22, 2016

(51) Int. Cl.
*C07D 319/00* (2006.01)
*A61K 38/00* (2006.01)
(Continued)

(52) U.S. Cl.
CPC ............ *C07D 319/22* (2013.01); *A61K 31/12* (2013.01); *A61K 31/357* (2013.01); *A61K 31/36* (2013.01); *C07D 317/70* (2013.01)

(58) Field of Classification Search
CPC .... C07D 319/22; C07D 319/00; C07C 45/59; C07C 49/784; C07C 253/80; C07C 255/56; C07C 317/70
(Continued)

(56) References Cited

U.S. PATENT DOCUMENTS

| 4,623,660 A * | 11/1986 | Richardson ............ C07C 45/46 514/428 |
| 2006/0084647 A1* | 4/2006 | Wang ...................... C07C 39/10 514/232.5 |
| 2006/0217389 A1* | 9/2006 | Sun ........................ A61K 31/42 514/252.05 |

FOREIGN PATENT DOCUMENTS

| CN | 103183598 | * 7/2013 |
| JP | 05112552 | * 7/1993 |

OTHER PUBLICATIONS

Kangani et al,Mild, Efficient Friedel-Crafts Acylations from Carboxylic Acids Using Cyanuric Chloride and AlCl3, Organic Letters, 2008, vol. 10, No. 13, p. 2645-2648.*
(Continued)

*Primary Examiner* — T. Victor Oh
(74) *Attorney, Agent, or Firm* — Idea Intellectual Limited; Margaret A. Burke; Sam T. Yip (57) ABSTRACT

This invention relates to the quick and efficient synthesis of anti-tumor or anti-cancer compounds. More particularly, it relates to the quick and efficient synthesis of anti-tumor or anti-cancer compounds comprising phenylacetophenone derivatives using oxabenzonorbornadienes with terminal alkynes.

14 Claims, 2 Drawing Sheets

(51) Int. Cl.
  *C07D 319/22*  (2006.01)
  *C07D 317/70*  (2006.01)
  *A61K 31/12*  (2006.01)
  *A61K 31/357*  (2006.01)
  *A61K 31/36*  (2006.01)

(58) Field of Classification Search
  USPC .......................................... 549/359; 514/19.3
  See application file for complete search history.

(56) References Cited

OTHER PUBLICATIONS

Soria-Castro et al, An Expedinet route to heterocycles through alpah-arylation of ketones and arylamides by microwave induced thermal SRN1 reactions, RSC Advances, 2014, 4(34), p. 17490-17497.*

Caturla et al, Synthesis and Biological Evalution of 2-Phenylpyran-4-ones: A new Class of Orally Active Cyclooxygenase-2 Inhibitors, Journal of Medicinal Chemistry, 2004, 47(15), p. 3874-3886.*

Yamamoto et al, Fries rearrangement of phenyl-1 and 2-naphthylacetates, Nippon Kagaku Kaishi, 1994, 8,p. 701-706 (an astract page).*

Jacubert et al, p-Toluenesulfonic acid-mediated cyclization of o-(1-alkynyl)anisoles or thioanisoles:synthesis of 2-aryl-substituted benzofurans and benzothiophenes,Tetrahedron Letters, 2009, 50(26), p. 3588-3592, an abstract page.*

Li et al, Synthesis and Photophysical Properties of Pyrrole/Polycyclic Aromatic Units Hybrid Fluorophores, J. Org., Chem. 2010,75, p. 4004-4013.*

Liu et al, Lewis base organocatalyzed enantioselective hydrosilylation of alpha-keto ketimines, Chemical Research in Chinese Universities , 2014, 30(2), p. 235-241, abstract page.*

Smith et al, Ring-chain tautomerism of 1-hydroxyphthalans. An examination of structural effects, Tetrahedron, 40(10), 1984, p. 1667-1672, abstract page.*

Fischer et al, Phenylpropargyl Radicals and Their Dimerization Products: An IR/UV Double Resonance Study, Journal of Physical Chemistry A, 2012, 116(33), p. 8515-8522.*

* cited by examiner

PALLADIUM/SILVER CO-CATALYZED TANDEM REACTIONS SYNTHESIS OF PHENYLACETOPHENONE DERIVATIVES BY OXABENZONORBORNADIENES WITH TERMINAL ALKYNES AND THEIR ANTI-TUMOR OR ANTI-CANCER ACTIVITIES

FIELD OF INVENTION

This invention relates to the synthesis of anti-tumor or anti-cancer compounds. More particularly, it relates to the synthesis of anti-tumor or anti-cancer compounds comprising phenylacetophenone derivatives using oxabenzonorbornadienes with terminal alkynes.

BACKGROUND OF INVENTION

Over the past few decades, a number of natural and synthetic compounds have been investigated for their possible anti-tumor or anti-cancer activities. However, as a consequence of frequent and excessive use of anti-tumor or anti-cancer agents, multidrug resistance and side effect have emerged and now cause severe clinical problems. Accordingly, there is an urgent and increasing need to discover and develop novel classes of anti-tumor or anti-cancer agents to make possible control of such multidrug resistance. It is the objective of the present invention to synthesize anti-tumor or anti-cancer compounds comprising phenylacetophenone derivatives using oxabenzonorbornadienes with terminal alkynes.

Citation or identification of any reference in this section or any other section of this application shall not be construed as an admission that such reference is available as prior art for the present application.

SUMMARY OF INVENTION

Accordingly, the objective of this invention is to provide anti-tumor or anti-cancer compounds for treating cancer and anti-tumor or anti-cancer compounds comprising phenylacetophenone derivatives based compounds.

In accordance with a first aspect of the present invention, there is provided anti-tumor or anti-cancer compounds for treating cancer synthesized via steps comprising:
  adding a Pd complex, a ligand and a first solvent in a first noble gas atmosphere to form a first mixture;
  stirring the first mixture at a first given temperature for a first given time duration;
  adding $CF_3SO_3Ag$ to the stirred first mixture to form a second mixture;
  stirring the second mixture for a second given time duration;
  adding an oxobenzonorbornadienes derivative and a second solvent to the stirred second mixture to form a third mixture;
  stirring the third mixture for a third given time duration;
  adding a terminal alkynes to the third mixture to form a fourth mixture;
  stirring the fourth mixture in a second noble gas atmosphere at a second given temperature until the complete consumption of the oxobenzonorbornadienes derivative;
  evaporating the solvents in the stirred fourth mixture to obtain residue; and
  purifying the residue to obtain the anti-tumor or anti-cancer compounds.

In a first embodiment of the first aspect of the present invention there is provided anti-tumor or anti-cancer compounds, being of a structure of formula (I) or formula (II):

wherein each of $R_1$, $R_2$, $R_3$, $R_4$ is selected from a group consisting of H, OH, $OCH_2CH_2O$, $OCH_2O$, $OCF_3$, $CF_3$, $CH_2CH_2OH$, aryl, aryloxyl, halogen, alkyl, alkenyl, alkynyl, hydroxyl, alkoxyl, amine and nitro groups; and wherein each of $R_5$, $R_6$, $R_7$, $R_8$, $R_9$ is selected from a group consisting of H, OH, $OCH_2CH_2O$, $OCH_2O$, $OCF_3$, $CF_3$, $CH_2CH_2OH$, aryl, aryloxyl, halogen, alkyl, alkenyl, alkynyl, hydroxyl, alkoxyl, amine, nitro, nitrile, alkylthio, alkyl sulfonyl, and aryl sulfonyl groups.

In a second embodiment of the first aspect of the present invention there is provided anti-tumor or anti-cancer compounds comprising 2-(naphthalen-2-yl)-1-phenylethanone;
1-(4-methoxyphenyl)-2-(naphthalen-2-yl) ethanone;
1-(2-methoxyphenyl)-2-(naphthalen-2-yl) ethanone;
1-(3-methoxyphenyl)-2-(naphthalen-2-yl) ethanone;
1-(3,5-dimethoxyphenyl)-2-(naphthalen-2-yl) ethanone;
1-(4-fluorophenyl)-2-(naphthalen-2-yl) ethanone;
2-(naphthalen-2-yl)-1-(4-(trifluoromethoxy) phenyl) ethanone;
1-(4-bromophenyl)-2-(naphthalen-2-yl) ethanone;
2-(naphthalen-2-yl)-1-(p-tolyl) ethanone;
2-(naphthalen-2-yl)-1-(4-phenoxyphenyl) ethanone;
1-(4-(hydroxymethyl)phenyl)-2-(naphthalen-2-yl) ethanone;
2-(naphthalen-2-yl)-1-(4-(trifluoromethyl) phenyl) ethanone;
4-(2-(naphthalen-2-yl) acetyl) benzonitrile;
2-(naphthalen-2-yl)-1-phenylethanone-2-D;
2-(5,8-dimethoxynaphthalen-2-yl)-1-phenylethanone;
2-(5,8-dimethylnaphthalen-2-yl)-1-phenylethanone;
2-(6,7-dimethylnaphthalen-2-yl)-1-phenylethanone;
2-(6,7-dibromonaphthalen-2-yl)-1-phenylethanone;
7-(phenylethynyl)-2,3-dihydronaphtho [2,3-b][1,4] dioxine; and
6-(phenylethynyl) naphtho [2,3-d][1,3] dioxole.

In a third embodiment of the first aspect of the present invention there is provided anti-tumor or anti-cancer compounds being of the structure of the chemical formula 3aa, 3ab, 3ac, 3ad, 3ae, 3af, 3ag, 3ah, 3ai, 3aj, 3ak, 3al, 3am, 3an, 3ba, 3ca, 3da, 3ea, 3ga, and 3ha:

3aa

3ab

3ac

3ad

3ae

3af

3ag

3ah

3ai

3aj

3ak

3al

3am

3an

3ba

-continued

3ca

3da

3ea

3ga

3ha

In a fourth embodiment of the first aspect of the present invention there is provided anti-tumor or anti-cancer compounds wherein the Pd complex comprises Pd(OAc)$_2$, C$_{10}$H$_{14}$O$_4$Pd, PdBr$_2$, Pd(CF$_3$COO)$_2$, Pd(C$_6$HF$_6$O$_2$)$_2$, PdCl$_2$, PdI$_2$, and C$_6$H$_{10}$Pd$_2$Cl$_2$.

In a fifth embodiment of the first aspect of the present invention there is provided anti-tumor or anti-cancer compounds wherein the ligand comprises (±)-Binap, Xantphos, DPEphos, Dppf, Dppb, and PPh$_3$.

In a sixth embodiment of the first aspect of the present invention there is provided anti-tumor or anti-cancer compounds wherein the first solvent comprises DCE, DCM, DME, THF, and Toluene.

In a seventh embodiment of the first aspect of the present invention there is provided anti-tumor or anti-cancer compounds wherein the second solvent comprises DCE, DCM, DME, THF, and Toluene.

In an eighth embodiment of the first aspect of the present invention there is provided anti-tumor or anti-cancer compounds wherein the first noble gas and/or second noble gas comprises argon gas.

In a ninth embodiment of the first aspect of the present invention there is provided anti-tumor or anti-cancer compounds wherein the first and/or second given temperature ranges between 34° C. to 76° C., and is preferably 55° C.

In a tenth embodiment of the first aspect of the present invention there is provided anti-tumor or anti-cancer compounds wherein the first and/or second given temperature is room temperature.

In an eleventh embodiment of the first aspect of the present invention there is provided anti-tumor or anti-cancer compounds wherein the first and/or second and/or third given time duration is at least 10 minutes.

In a twelfth embodiment of the first aspect of the present invention there is provided anti-tumor or anti-cancer compounds wherein the oxobenzonorbornadienes derivative is of a structure of formula (III):

wherein R$_1$ is selected from a group consisting of H, OMe, Me, OCH$_2$CH$_2$O, OCH$_2$O, Ph, and OPh; R$_2$ is selected from a group consisting of H, Me, Br, Cl, F, OCH$_2$, OMe, OCH$_2$CH$_2$O, OCH$_2$O, Ph, and OPh; R$_3$ is selected from a group consisting of H, Me, Br, Cl, F, CH$_2$O, O, OMe, OCH$_2$CH$_2$O, OCH$_2$O, Ph, and OPh; and R$_4$ is selected from a group consisting of H, OMe, Me, OCH$_2$CH$_2$O, OCH$_2$O, Ph, and OPh.

In a thirteenth embodiment of the first aspect of the present invention there is provided anti-tumor or anti-cancer compounds wherein the terminal alkynes is of a structure of formula (IV):

wherein R$_1$ is selected from a group consisting of H and D; and R$_2$ is selected from a group consisting of Ph, 4-MeOC$_6$H$_4$, 2-MeOC$_6$H$_4$, 3-MeOC$_6$H$_4$, 3,5-diMeOC$_6$H$_3$, 4-FC$_6$H$_4$, 4-PhOC$_6$H$_4$, 4-CF$_3$OC$_6$H$_4$, 4-BrC$_6$H$_4$, 4-MeC$_6$H$_4$, 4-OHCH$_2$C$_6$H$_4$, 4-CF$_3$C$_6$H$_4$ and 4-CNC$_6$H$_4$.

In a fourteenth embodiment of the first aspect of the present invention there is provided anti-tumor or anti-cancer compounds wherein the evaporation method comprises vacuum evaporation.

In a fifteenth embodiment of the first aspect of the present invention there is provided anti-tumor or anti-cancer compounds wherein the purification method comprises silica gel column chromatography.

In a sixteenth embodiment of the first aspect of the present invention there is provided anti-tumor or anti-cancer compounds wherein the cancer treated comprises gastric cancer, colon cancer, esophageal cancer and liver cancer.

In a second aspect of the present invention there is provided anti-tumor or anti-cancer compounds comprising phenylacetophenone derivatives based compounds.

In a first embodiment of the second aspect of the present invention there is provided anti-tumor or anti-cancer compounds comprising 2-(naphthalen-2-yl)-1-phenylethanone; 1-(4-methoxyphenyl)-2-(naphthalen-2-yl) ethanone; 1-(2-methoxyphenyl)-2-(naphthalen-2-yl) ethanone; 1-(3-methoxyphenyl)-2-(naphthalen-2-yl) ethanone; 1-(3,5-dimethoxyphenyl)-2-(naphthalen-2-yl) ethanone; 1-(4-fluorophenyl)-2-(naphthalen-2-yl) ethanone;

2-(naphthalen-2-yl)-1-(4-(trifluoromethoxy) phenyl) ethanone;
1-(4-bromophenyl)-2-(naphthalen-2-yl) ethanone;
2-(naphthalen-2-yl)-1-(p-tolyl) ethanone;
2-(naphthalen-2-yl)-1-(4-phenoxyphenyl) ethanone;
1-(4-(hydroxymethyl)phenyl)-2-(naphthalen-2-yl) ethanone;
2-(naphthalen-2-yl)-1-(4-(trifluoromethyl) phenyl) ethanone;
4-(2-(naphthalen-2-yl) acetyl) benzonitrile;
2-(naphthalen-2-yl)-1-phenylethanone-2-D;
2-(5,8-dimethoxynaphthalen-2-yl)-1-phenylethanone;
2-(5,8-dimethylnaphthalen-2-yl)-1-phenylethanone;
2-(6,7-dimethylnaphthalen-2-yl)-1-phenylethanone;
2-(6,7-dibromonaphthalen-2-yl)-1-phenylethanone;
7-(phenylethynyl)-2,3-dihydronaphtho [2,3-b][1,4] dioxine; and
6-(phenylethynyl) naphtho [2,3-d][1,3] dioxole.

In a second embodiment of the second aspect of the present invention there is provided anti-tumor or anti-cancer compounds, being of a structure of the chemical formula 3aa, 3ab, 3ac, 3ad, 3ae, 3af, 3ag, 3ah, 3ai, 3aj, 3ak, 3al, 3am, 3an, 3ba, 3ca, 3da, 3ea, 3ga, and 3ha:

3aa

3ab

3ac

3ad

3ae

3af

3ag

3ah

3ai

3aj

3ak

3al

3am

3an

3ba
3ca
3da
3ea
3ga
3ha

In a third embodiment of the second aspect of the present invention there is provided anti-tumor or anti-cancer compounds wherein the cancer treated comprises gastric cancer, colon cancer, esophageal cancer and liver cancer.

Those skilled in the art will appreciate that the invention described herein is susceptible to variations and modifications other than those specifically described.

The invention includes all such variations and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

The present invention is not to be limited in scope by any of the specific embodiments described herein. The following embodiments are presented for exemplification only.

Phenylacetophenone is common skeleton, which has many interesting biological activities, including protein tyrosine phosphatase inhibitory activity, and anti-microbial activity. In recent years, this class of compounds came to receive increasing attention from chemists. As reported, the major synthesis methods of phenylacetophenone were thansition-metal-catalyzed arylation of ketones, silyyl enol ethers and vinylic acetates with aryl halides; hydration of alkynes; and addition of aryl to nitriles. The transition metal-catalyzed reactions of oxabenzonorbornadienes have attracted continuous interest and extensive study in recent years. Our group has had a continuing interest in the transition metal-catalyzed reactions of oxabenzonorbornadienes with terminal alkynes for several years. Recently, we reported several efficient methods using transition metal-catalyzed resulted ring opening reaction of oxabenzonorbornadienes with terminal alkynes. The method followed realized the non-ring opening reaction by a palladium/silver/ligand co-catalyzed tandem reactions of oxabenzonorbornadienes with terminal alkynes. As mentioned above, our findings developed a new way to synthesize phenylacetophenone with good yield. Further biological activities screening was based on the tandem reactions products by the MTT method.

Result and Discussion

Some phosphine ligands were examined in the tandem reaction of oxabenzonorbornadiene. Table 1 shows the tandem reaction of oxabenzonorbornadiene 1a with phenylacetylene 2a (3 equiv) in the presence of Pd complexes generated by Pd(OAc)$_2$ and phosphine ligands in the presence of AgOTf. The result indicated that (rac)-Binap, Xantphos and DPEphos all gave good yields (62-79% yields, entry 1-3), while DPPF, DPPB and PPh$_3$ were not efficient in this reaction (entry 4-6). It could be seen that (rac)-Binap resulted in the best yield. Other palladium pre-catalysis in combination with (rac)-Binap were also investigated in the invention. Most of palladium precursors could promote the reaction to give good yields (54-78% yields, entry 7-12) under the same conditions, but C$_6$H$_{10}$Pd$_2$Cl$_2$ showed lower catalytic activity (27% yield). Pd(OAc)$_2$ was found to be the most effective.

TABLE 1

Ligand and palladium screening of palladium-catalyzed tandem reaction of oxabenzonorbornadienes[a].

| Entry | [M] | Ligand | Time (h) | Yield (%)[b] |
|---|---|---|---|---|
| 1 | Pd(OAc)$_2$ | (±)-Binap | 22 | 79 |
| 2 | Pd(OAc)$_2$ | Xantphos | 27 | 75 |
| 3 | Pd(OAc)$_2$ | DPEphos | 4 | 62 |
| 4 | Pd(OAc)$_2$ | Dppf | 48 | Trace |
| 5 | Pd(OAc)$_2$ | Dppb | 48 | Trace |
| 6 | Pd(OAc)$_2$ | PPh$_3$ | 48 | Trace |
| 7 | C$_{10}$H$_{14}$O$_4$Pd | (±)-Binap | 22 | 78 |
| 8 | PdBr$_2$ | (±)-Binap | 36 | 63 |
| 9 | Pd(CF$_3$COO)$_2$ | (±)-Binap | 5 | 54 |
| 10 | Pd(C$_6$HF$_6$O$_2$)$_2$ | (±)-Binap | 22 | 67 |
| 11 | PdCl$_2$ | (±)-Binap | 36 | 65 |
| 12 | PdI$_2$ | (±)-Binap | 17 | 71 |
| 13 | C$_6$H$_{10}$Pd$_2$Cl$_2$ | (±)-Binap | 46 | 27 |

[a]Reaction conditions: 2a (0.9 mmol), 2a:1a:[Pd]:Ligand:[Ag] (3:1:0.015:0.018:0.03) in THF (2 mL) at 35° C. under Ar$_2$ for indicated period of time
[b]Isolated yields.

Thus, Pd(OAc)$_2$ and (rac)-Binap were chosen to investigate solvent and temperature effect (Table 2). Among the test solvents, DME, dioxane and toluene were more effective (79-86% yields, entries 3-6) than DCE and DCM (entries 1-2) in this reaction. Toluene was the best suitable solvent (entry 6). The dosage of ligand had a strong impact on the yield. For example, using 3 mol % (rac)-Binap could get 97% yield for 1 h (entry 7). But, increasing (rac)-Binap to 9 mol %, the yield of product decreased to 70% (entry 8). The temperature examinations showed the reaction temperature of 55° C. to be optimal (entry 11).

TABLE 2

Optimization of reaction conditions[a]

| Entry | Solvent | Temp (° C.) | Time (h) | Yield (%)[b] |
|---|---|---|---|---|
| 1 | DCE | 35 | 2 | Complex |
| 2 | DCM | 35 | 2 | Complex |
| 3 | DME | 35 | 2 | 81% |
| 4 | THF | 35 | 22 | 79% |
| 5 | Dioxane | 35 | 2 | 79% |
| 6 | Toluene | 35 | 2 | 86% |
| 7[c] | Toluene | 35 | 1.5 | 97% |
| 8[d] | Toluene | 35 | 1.5 | 70% |
| 9 | Toluene | rt | 17 | 96% |
| 10 | Toluene | 35 | 2 | 97% |
| 11 | Toluene | 55 | 1 | 99% |
| 12 | Toluene | 75 | 0.5 | 87% |

[a]Reaction conditions: 2a (0.9 mmol), 2a:1a:[Pd]:[Ag] (3:1:0.015:0.03), in (2 mL) solvent under Ar$_2$ for indicated period of time.
[b]Isolated yields.
[c]Used 3 mol % (±)-Binap.
[d]Used 9 mol % (±)-Binap The results of the tandem reaction of a variety of terminal alkynes 2a-n to oxabenzonorbornadiene 1a in the presence of Pd(OAc)$_2$ (5.0% mol)/AgOTf (10.0% mol) and (rac)-Binap (3.0% mol) in toluene at 55° C. are summarized in Table 3. Generally, all terminal aromatic alkynes reacted with 1a smoothly to provide the corresponding products in excellent yields (entries 1-14). The electronic properties of the substituents for aromatic rings of terminal alkynes 2a-n were well tolerated by this tandem reaction. In particular, the terminal alkyne with —CH$_2$OH on aromatic ring afforded high yield (90%) (entry 11).

TABLE 3

Pd-catalyzed asymmetric rearrangement reaction of 1a with various terminal alkynes[a]

| Entry | R$_1$, R$_2$ | 2 | Time (h) | Yield (%)[b] |
|---|---|---|---|---|
| 1 | H, Ph | 2a | 1 | 99 |
| 2 | H, 4-MeOC$_6$H$_4$ | 2b | 1 | 91 |
| 3 | H, 2-MeOC$_6$H$_4$ | 2c | 1 | 90 |

TABLE 3-continued

| | | | | |
|---|---|---|---|---|
| 4 | H, 3-MeOC$_6$H$_4$ | 2d | 1 | 99 |
| 5 | H, 3, 5-diMeOC$_6$H$_3$ | 2e | 20 min | 92 |
| 6 | H, 4-FC$_6$H$_4$ | 2f | 0.5 | 98 |
| 7 | H, 4-PhOC$_6$H$_4$ | 2g | 1 | 98 |
| 8 | H, 4-CF$_3$OC$_6$H$_4$ | 2h | 0.5 | 90 |
| 9 | H, 4-BrC$_6$H$_4$ | 2i | 1 | 99 |
| 10 | H, 4-MeC$_6$H$_4$ | 2j | 1 | 92 |
| 11 | H, 4-OHCH$_2$C$_6$H$_4$ | 2k | 1 | 90 |
| 12 | H, 4-CF$_3$C$_6$H$_4$ | 2l | 0.5 | 93 |
| 13 | H, 4-CNC$_6$H$_4$ | 2m | 13 | 98 |
| 14 | D, Ph | 2n | 2 | 95 |

[a]Reaction conditions: 2a (0.6 mmol), 2a:1a:[Pd]:Ligand:[Ag] (3:1:0.015:0.009:0.03), in Toluene (2 mL) at 55° C. under Ar for indicated period of time.
[b]Isolated yield by column chromatography.

To extend the scope of substrates, substituted oxabenzo-norbornadiene derivatives 1a-e were examined. As shown in Table 4, the tandem reaction of oxabenzonorbornadienes 1a-e with phenylacetylene 2a proceeded smoothly to afford the corresponding products in good yields.

TABLE 4

Pd-catalyzed asymmetric rearrangement reaction of substituted Oxabenzonorbornadienes with phenylacetylene 2a[a]

| Entry | R$_1$, R$_2$, R$_3$, R$_4$ | 1 | Time (h) | Yield (%)[b] |
|---|---|---|---|---|
| 1 | H, H, H, H | 1a | 1 | 99 |
| 2 | OMe, H, H, OMe | 1b | 0.5 | 56 |
| 3 | Me, H, H, Me | 1c | 3 | 97 |
| 4 | H, Me, Me, H | 1d | 3 | 91 |
| 5 | H, Br, Br, H | 1e | 0.5 | 89 |

[a]Reaction conditions: 2a (0.6 mmol), 2a:1a:[Pd]:Ligand:[Ag] (3:1:0.015:0.009:0.03), in Toluene (2 mL) at 55° C. under Ar for indicated period of time.
[b]Isolated yield by column chromatography.

To our delight, we could get another kind of product in good yields when we employed oxabenzonorbornadiene derivatives 1g-h as substrates to react with phenylacetylene 2a.

TABLE 5

The use of electron-donating 1 in this Pd/Ag catalytic system[a].

| Entry | R$_1$, R$_2$, R$_3$, R$_4$ | 1 | Time (h) | Yield (%)[b] |
|---|---|---|---|---|
| 1 | H, OCH$_2$CH$_2$O, H | 1g | 1 | 90 |
| 2 | H, OCH$_2$O, H | 1h | 0.5 | 77 |

[a]Reaction conditions: 2a (0.6 mmol), 2a:1a:[Pd]:Ligand:[Ag] (3:1:0.015:0.009:0.03), in Toluene (2 mL) at 55° C. under Ar for indicated period of time.
[b]Isolated yield by column chromatography.

The palladium/AgOTf co-catalyzed tandem reactions of oxabenzonorbornadienes were developed with terminal alkynes in good to excellent yields. Further biological activities screening was based on the products catalyzed by this catalysis.

Cytotoxic activities of all compounds were evaluated by MTT assay using KYSE-150 (human oesophagus carcinoma), MKN-45 (human gastric aednocarcinoma), DLD-1 (human colorectal carcinoma cell line), Hep G2 (human hepatocellular carcinoma). IC$_{50}$ values were shown in Table 6. As shown in Table 6, 3ab, 3af, 3ai had strong cell growth-inhibiting effects against all test cell lines for which IC$_{50}$ values are below or near 10 μM. 3ag, 3al, 3an, 3ea and 3ha also have the same inhibitory effect on different cell lines with IC$_{50}$ value lower than 10 μM. Thus, except 3ac, 3ad, 3ae, 3ah, and 3ab, the other compounds all exert definitely anti-cancer effect.

TABLE 6

Cytotoxicity of compounds against cancer cell lines[a]

| Compound | KYSE-150 | MKN-45 | Hep G2 | DLD-1 |
|---|---|---|---|---|
| 3aa | 10.94 | 15.58 | 20.76 | 12.36 |
| 3ab | 5.19 | 10.09 | 7.63 | 7.89 |
| 3ac | >50 | >50 | >50 | >50 |
| 3ad | >50 | >50 | >50 | >50 |
| 3ha | 3.52 | 20.8 | 0.65 | 0.55 |
| 3ae | >50 | >50 | 42.78 | >50 |
| 3af | 2.56 | 4.04 | 4.23 | 5.27 |
| 3ah | >50 | >50 | >50 | >50 |
| 3ai | 2.02 | 4.45 | 1.32 | 3.3 |
| 3aj | 18.37 | 11.99 | >50 | >50 |
| 3ag | 1.19 | >50 | 4.84 | 4.95 |
| 3ak | 31.34 | >50 | >50 | 48.24 |
| 3al | 4.75 | >50 | 29.95 | 37.38 |
| 3am | 33.46 | >50 | >50 | >50 |
| 3ca | 19.23 | >50 | >50 | >50 |

TABLE 6-continued

Cytotoxicity of compounds against cancer cell lines[a]

| Compound | KYSE-150 | MKN-45 | Hep G2 | DLD-1 |
|---|---|---|---|---|
| 3ga | 24.65 | 35.15 | 45.18 | 19.71 |
| 3da | 7.69 | 3.71 | >50 | 0.78 |
| 3ba | >50 | >50 | >50 | >50 |
| 3ea | 2.38 | 12.07 | 16.09 | 2.7 |
| 3an | 7.43 | 43.14 | 22 | >50 |

[a]Results are expressed as $IC_{50}$ values in μM.

Figure 1:
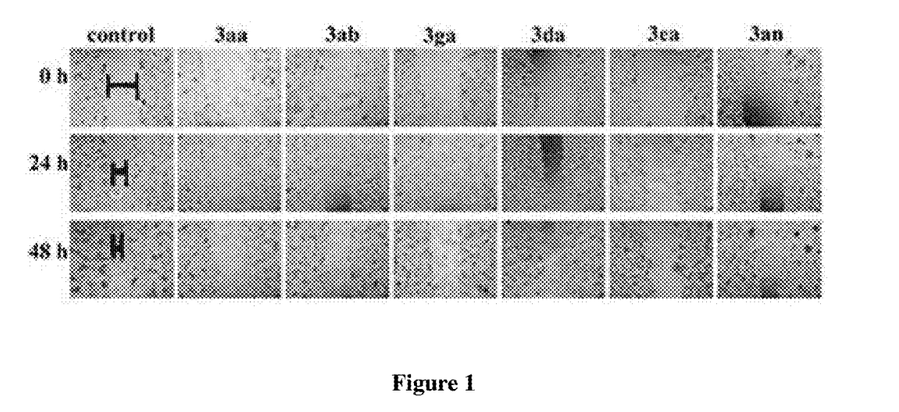
FIG. 1 shows wound healing assay of seven novel compounds on human esophageal carcinoma (KYSE-150) cells; 10 μM of 3aa, 3ab, 3ga, 3ea, 3an and 5 μM of 3da were used to treat the cancer cells for 48 h. Original magnification, 5×.
Figure 2:
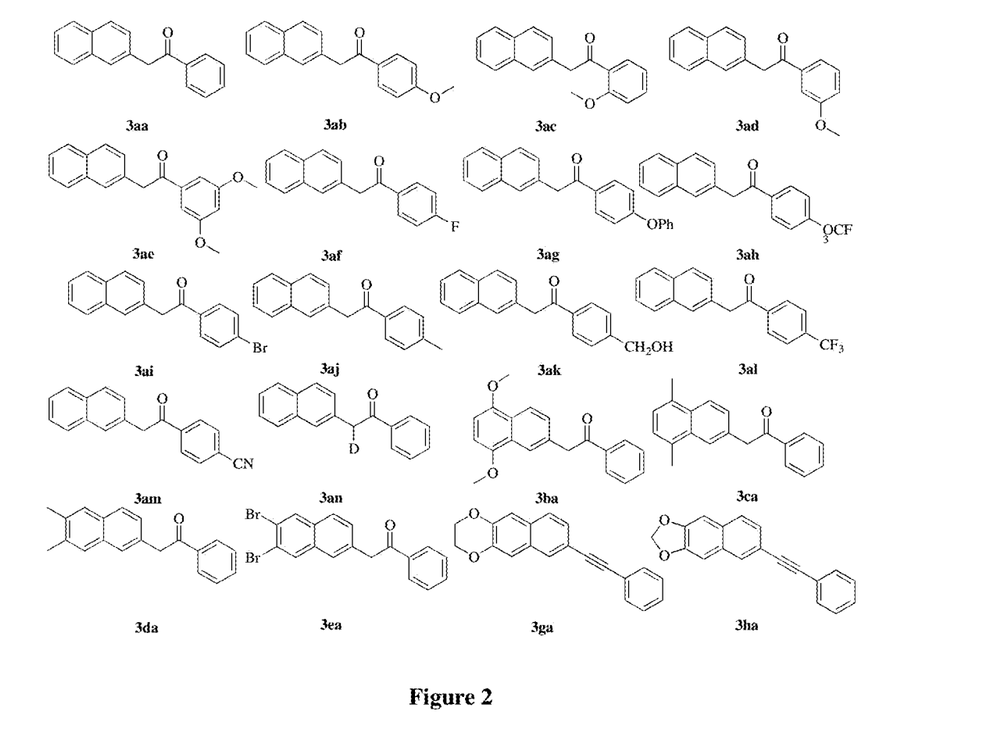
FIG. 2 shows structure of all the compounds.

Further, wound-healing assay was used to test whether those novel compounds could affect cell motility. A confluent monolayer of KYSE-150 cells was scratched to form a wound and incubated in the absence or presence of tested compounds at the concentrations of 5 and 10 μM (5 μM of 3da and 10 μM of 3aa, 3ab, 3ga, 3ea, 3an were tested and did not alter the viability of KYSE-150 cells as compared to that of controls). After 48 h, the wound edges were indistinguishable in control group, while compounds 3aa, 3ab, 3ga, 3da, 3ea and 3an treated cells did not migrate into the wound (FIG. 1), indicating that they had anti-migration effect on KYSE-150 cells in the absence of cytotoxicity.

Experimental Section

General Method

The reactions and manipulations were performed under an atmosphere of argon by using standard Schlenk techniques and Drybox (Mikrouna, Supper 1220/750). Anhydrous toluene, DME, THF and dioxane were distilled from sodium benzophenone ketyl prior to use. Anhydrous toluene was distilled from calcium hydride and stored under argon. Absolute MeOH and isopropyl alcohol were distilled from magnesium and stored under argon. $^1$H NMR and $^{13}$C NMR spectra were recorded on Bruker-Avance 400 MHz spectrometer. $CDCl_3$ was used as solvent. Chemical shifts (δ) were reported in ppm with tetramethylsilane as internal standard, and J values were given in Hz. High resolution mass spectra (HRMS) were performed on a VG Autospec-3000 spectrometer. Column chromatography was performed with silica gel (200-300 mesh).

Synthesis of Substrates

Oxobenzonorbornadienes 1a, 1b, 1c, 1d, 1e, 1f, 1g, 1h, and 1i were prepared by the literature procedures.

Procedure for Pd-Catalyzed Asymmetric Ring-Opening Reaction of Oxobenzonorbornadienes with Various Terminal Alkynes by Lewis Acid $Pd(OAc)_2$ (3.4 mg, 0.015 mmol), (±)-Binap (5.6 mg, 0.009 mmol) and 1.0 mL toluene were added to a Schlenk tube in argon atmosphere. The resulting solution was stirred at room temperature for 30 min, then a solution of $CF_3SO_3Ag$ (7.7 mg, 0.03 mmol) was added, and the mixture was stirred for additional 10 min. After the addition of Oxabenzonor-bornadiene 1a (43.2 mg, 0.3 mmol) in toluene (1.0 mL) was added, the mixture was stirred for additional 10 min. The last addition of Terminal alkyne 2a (67 μl, 0.6 mmol), the mixture was stirred at 55° C. under argon atmosphere with TLC monitoring until the complete consumption of 1a. After vacuum evaporation of the solvent, the residue was purified by silica gel column chromatography to provide the desired product 3aa (73.1 mg, 99% yield).

2-(naphthalen-2-yl)-1-phenylethanone (3aa)

Yellow solid, 99% yield, m.p. 122-124° C. $^1$H NMR (400 MHz, $CDCl_3$): δ 8.10-8.02 (d, J=7.4 Hz, 2H), 7.85-7.78 (t, J=9.6 Hz, 3H), 7.74 (s, 1H), 7.58-7.54 (t, J=7.4 Hz, 1H), 7.51-7.44 (m, 4H), 7.43-7.39 (m, 1H), 4.46 (s, 2H). $^{13}$C NMR (100 MHz, $CDCl_3$) δ 197.63, 136.67, 133.61, 133.19, 132.42, 132.16, 128.67, 128.33 128.12, 127.68, 127.64, 127.65, 127.59, 126.12, 125.75, 45.72; HRMS calcd for $C_{18}H_{14}O$ $[M+1]^+$: 246.1045. Found: 246.1052.

1-(4-methoxyphenyl)-2-(naphthalen-2-yl) ethanone (3ab)

Light yellow solid, 91% yield, m.p. 125-127° C. $^1$H NMR (400 MHz, $CDCl_3$) δ 8.09-7.99 (d, J=8.9 Hz, 2H), 7.85-7.76 (t, J=8.7 Hz, 3H), 7.72 (s, 1H), 7.56-7.42 (m, 2H), 7.42-7.35 (m, 1H), 7.00-6.83 (d, J=8.9 Hz, 2H), 4.40 (s, 2H), 3.85 (s, 3H). $^{13}$C NMR (100 MHz, $CDCl_3$) δ 196.32, 163.55, 133.57, 132.57, 132.34, 131.04, 129.60, 128.30, 127.98, 127.67, 127.64, 127.57, 126.09, 125.69, 113.83, 55.50, 45.53; HRMS calcd for $C_{19}H_{16}O_2$ $[M+1]^+$: 276.1150. Found: 276.1156.

1-(2-methoxyphenyl)-2-(naphthalen-2-yl) ethanone (3ac)

White solid, 90% yield, m.p. 100-102° C. $^1$H NMR (400 MHz, $CDCl_3$) δ 7.83-7.76 (m, 3H), 7.74-7.67 (m, 2H), 7.49-7.42 (m, 3H), 7.41-7.36 (m, 1H), 7.02-6.94 (m, 2H), 4.50-4.47 (d, J=4.7 Hz, 2H), 3.94-3.92 (d, J=2 Hz, 3H). $^{13}$C NMR (100 MHz, $CDCl_3$) δ 200.12, 158.49, 133.66, 133.55, 132.88, 132.33, 130.75, 128.21, 128.20, 128.13, 127.89, 127.66, 125.91, 125.52, 120.78, 111.54, 55.51, 50.36; HRMS calcd for $C_{19}H_{16}O_2$ $[M+1]^+$: 276.1150. Found: 276.1150.

1-(3-methoxyphenyl)-2-(naphthalen-2-yl) ethanone (3ad)

White solid, 99% yield, m.p. 102-103° C. $^1$H NMR (400 MHz, $CDCl_3$) δ 7.84-7.77 (t, J=8.3 Hz, 3H), 7.72 (s, 1H), 7.67-7.61 (d, J=7.7 Hz, 1H), 7.58-7.53 (t, J=2.0 Hz, 1H), 7.51-7.42 (m, 2H), 7.42-7.31 (m, 2H), 7.16-7.05 (m, 1H), 4.43 (s, 2H), 3.83 (s, 3H). $^{13}$C NMR (100 MHz, $CDCl_3$) δ 197.49, 159.80, 137.87, 133.51, 132.33, 132.09, 129.62, 128.30, 128.06, 127.64, 127.61, 127.53, 126.10, 125.73, 121.33, 119.70, 112.78, 55.40, 45.79; HRMS calcd for $C_{19}H_{16}O_2$ $[M+1]^+$: 276.1150. Found: 276.1157.

1-(3,5-dimethoxyphenyl)-2-(naphthalen-2-yl) ethanone (3ae)

Light yellow solid, 92% yield, m.p. 70-71° C. $^1$H NMR (400 MHz, $CDCl_3$) δ 7.82-7.76 (m, 3H), 7.71 (s, 1H), 7.47-7.42 (m, 2H), 7.41-7.36 (m, 1H), 7.19-7.16 (d, J=2.3 Hz, 2H), 6.65-6.61 (t, J=2.3 Hz, 1H), 4.39 (s, 2H), 3.80 (s, 6H). $^{13}$C NMR (100 MHz, $CDCl_3$) δ 197.33, 160.82, 138.42, 133.52, 132.33, 132.07, 128.31, 128.05, 12127.64, 127.62, 127.51, 126.10, 125.73, 106.47, 105.36, 5.54, 45.79; HRMS calcd for $C_{20}H_{18}O_3$ $[M+1]^+$: 306.1256. Found: 306.1248.

1-(4-fluorophenyl)-2-(naphthalen-2-yl) ethanone (3af)

Red solid, 98% yield, m.p. 145-147° C. $^1$H NMR (400 MHz, CDCl$_3$) δ 8.10-8.05 (m, 2H), 7.84-7.78 (m, 3H), 7.72 (s, 1H), 7.49-7.44 (m, 2H), 7.41-7.37 (m, 1H), 7.15-7.10 (t, J=8.7 Hz, 2H): 4.42 (s, 2H). $^{13}$C NMR (100 MHz, CDCl$_3$) δ 196.08, 167.01, 164.47, 133.52, 132.91, 132.88, 132.36, 131.86, 131.36, 131.27, 128.41, 128.03, 127.67, 127.60, 127.40, 126.19, 125.82, 115.90, 115.68, 45.70; HRMS calcd for C$_{18}$H$_{13}$FO [M+1]$^+$: 264.0950. Found: 264.0959.

2-(naphthalen-2-yl)-1-(4-(trifluoromethoxy) phenyl) ethanone (3ah)

Light yellow solid, 90% yield, m.p. 153-154° C. $^1$H NMR (400 MHz, CDCl$_3$) δ 8.18-8.04 (d, J=9.0 Hz, 2H), 7.86-7.76 (m, 3H), 7.72 (s, 1H), 7.51-7.43 (m, 2H), 7.42-7.36 (m, 1H), 7.31-7.26 (d, J=8.7 Hz, 2H), 4.44 (s, 2H). $^{13}$C NMR (100 MHz, CDCl$_3$) δ 196.09, 152.65, 134.65, 133.52, 132.40, 131.60, 130.70, 128.50, 128.07, 127.69, 127.61, 127.35, 126.25, 125.89, 121.52, 120.41, 118.95, 45.80; HRMS calcd for C$_{19}$H$_{13}$F$_3$O$_2$ [M+1]$^+$: 330.0868. Found: 330.0873.

1-(4-bromophenyl)-2-(naphthalen-2-yl) ethanone (3ai)

Red solid, 99% yield, m.p. 157-159° C. $^1$H NMR (400 MHz, CDCl$_3$) δ 7.92-7.88 (d, J=8.6 Hz, 2H), 7.83-7.77 (m, 3H), 7.70 (s, 1H), 7.62-7.57 (d, J=8.6 Hz, 2H), 7.49-7.43 (m, 2H), 7.39-7.35 (m, 1H), 4.41 (s, 2H). $^{13}$C NMR (100 MHz, CDCl$_3$) δ 196.65, 135.78, 133.51, 132.37, 131.98, 131.66, 130.18, 128.45, 128.06, 127.67, 127.60, 127.36, 126.22, 125.86, 45.73; HRMS calcd for C$_{18}$H$_{13}$BrO$_2$ [M+1]$^+$: 324.0150. Found: 324.0159.

2-(naphthalen-2-yl)-1-(p-tolyl) ethanone (3aj)

Yellow solid, 92% yield, m.p. 144-146° C. $^1$H NMR (400 MHz, CDCl$_3$) δ 7.97-7.77 (d, J=8.2 Hz, 2H), 7.82-7.76 (t, J=8.8 Hz, 3H), 7.72 (s, 1H), 7.47-7.42 (m, 2H), 7.41-7.38 (m, 1H), 7.27-7.23 (d, J=5.8 Hz, 2H), 4.42 (s, 2H), 2.39 (s, 3H). $^{13}$C NMR (100 MHz, CDCl$_3$) δ 197.36, 144.06, 134.00, 133.51, 132.31, 132.29, 129.34, 128.79, 128.56, 128.02, 127.63, 127.60, 127.56, 126.05, 125.67, 45.61, 21.66; HRMS calcd for C$_{19}$H$_{16}$O [M+1]$^+$: 260.1201. Found: 260.1208.

2-(naphthalen-2-yl)-1-(4-phenoxyphenyl) ethanone (3ag)

Yellow solid, 98% yield, m.p. 139-141° C. $^1$H NMR (400 MHz, CDCl$_3$) δ 8.04-8.00 (m, 2H), 7.82-7.76 (t, J=8.4 Hz; 3H), 7.71 (s, 1H), 7.47-7.42 (m, 2H), 7.41-7.35 (t, J=7.8 Hz, 3H), 7.21-7.16 (t, J=7.2 Hz, 1H), 7.07-7.02 (d, J=7.8 Hz, 2H), 7.00-6.95 (m, 2H), 4.39 (s, 2H). $^{13}$C NMR (100 MHz, CDCl$_3$) δ 196.29, 162.14, 155.33, 133.58, 132.37, 132.34, 131.10, 131.04, 130.10, 128.38, 128.02, 127.70, 127.66, 127.52, 126.16, 125.77, 124.73, 120.32, 117.28, 45.66; HRMS calcd for C$_{24}$H$_{18}$O$_2$ [M+1]$^+$: 338.1307. Found: 260.1208.

1-(4-(hydroxymethyl)phenyl)-2-(naphthalen-2-yl) ethanone (3ak)

Yellow solid, 98% yield, m.p. 97-98° C. $^1$H NMR (400 MHz, CDCl$_3$) δ 8.07-8.02 (d, J=8.0 Hz, 2H), 7.82-7.77 (t, J=9.7 Hz, 3H), 7.72 (s, 1H), 7.48-7.43 (t, J=3.8 Hz, 4H), 7.42-7.38 (m, 1H), 7.46 (s, 2H), 7.44 (s, 2H), 1.77 (s, 1H). $^{13}$C NMR (100 MHz, CDCl$_3$) δ 197.33, 135.84, 133.58, 132.39, 132.12, 129.01, 128.64, 128.34, 128.08, 127.66, 127.63, 127.52, 126.71, 126.63, 126.13, 125.75, 64.65, 64.62, 45.78; HRMS calcd for C$_{19}$H$_{16}$O$_2$ [M+1]$^+$: 276.1150. Found: 276.1145.

2-(naphthalen-2-yl)-1-(4-(trifluoromethyl) phenyl) ethanone (3al)

Red solid, 93% yield, m.p. 179-181° C. $^1$H NMR (400 MHz, CDCl$_3$) δ 8.16-8.11 (d, J=8.2 Hz, 2H), 7.84-7.77 (m, 3H), 7.74-7.68 (m, 3H), 7.50-7.43 (m, 2H), 7.40-7.35 (m, 1H), 4.46 (s, 2H). $^{13}$C NMR (100 MHz, CDCl$_3$) δ 196.67, 139.09, 134.58, 134.26, 133.51, 132.41, 131.29, 128.97, 128.55, 128.15, 127.70, 127.61, 127.32, 126.29, 125.96, 125.80, 125.76, 125.73, 125.69, 124.87, 112.16, 46.00; HRMS calcd for C$_{19}$H$_{13}$F$_3$O [M+1]$^+$: 314.0918. Found: 314.0929.

4-(2-(naphthalen-2-yl) acetyl) benzonitrile (3am)

Light yellow solid, 98% yield, m.p. 152-154° C. $^1$H NMR (400 MHz, CDCl$_3$) δ 8.14-8.10 (d, J=8.2 Hz, 2H), 7.85-7.74 (m, 5H), 7.70 (s, 1H), 7.50-7.44 (m, 2H), 7.38-7.34 (m, 1H), 4.46 (s, 2H). $^{13}$C NMR (100 MHz, CDCl$_3$) δ 196.27, 139.38, 133.48, 132.56, 132.43, 130.93, 129.04, 128.65, 128.14, 127.71, 127.59, 127.19, 126.37, 126.04, 117.89, 116.40, 46.02; HRMS calcd for C$_{19}$H$_{13}$NO [M+1]$^+$: 271.0997. Found: 271.1003.

2-(naphthalen-2-yl)-1-phenylethanone-2-D (3an)

Red solid, 95% yield, m.p. 129-130° C. $^1$H NMR (400 MHz, CDCl$_3$) δ 8.09-8.03 (d, J=8.0 Hz, 2H), 7.84-7.78 (t, J=9.7 Hz, 3H), 7.73 (s, 1H), 7.58-7.53 (t, J=7.5 Hz, 1H), 7.49-7.44 (m, 4H), 7.43-7.39 (d, J=9.0 Hz, 1H), 4.57-4.25 (d, J=11 Hz, 1H). $^{13}$C NMR (100 MHz, CDCl$_3$) δ 197.70, 136.63, 133.59, 133.20, 132.40, 132.10, 128.68, 128.34, 128.09, 127.67, 127.64, 127.54, 126.12, 125.74, 45.72; HRMS calcd for C$_{18}$H$_{13}$DO [M+1]$^+$: 247.1107. Found: 247.1118.

2-(5,8-dimethoxynaphthalen-2-yl)-1-phenylethanone (3ba)

Yellow solid, 56% yield, m.p. 145-146° C. $^1$H NMR (400 MHz, CDCl$_3$) δ 8.19-8.15 (d, J=8.8 Hz, 1H), 8.13-8.10 (m, 1H), 8.07-8.02 (m, 2H), 7.56-7.51 (m, 1H), 7.47-7.40 (m, 3H), 6.70-6.65 (m, 2H), 4.46 (s, 2H), 3.94 (s, 6H). $^{13}$C NMR (100 MHz, CDCl$_3$) δ 197.71, 149.50, 149.22, 136.61, 133.09, 132.21, 128.67, 128.60, 127.41, 126.46, 125.24, 122.36, 122.20, 103.52, 103.09, 55.72, 55.66, 46.00; HRMS calcd for C$_{20}$H$_{18}$O$_3$ [M+1]$^+$: 306.1256. Found: 306.1253.

2-(5,8-dimethylnaphthalen-2-yl)-1-phenylethanone (3ca)

White solid, 97% yield, m.p. 123-124° C. $^1$H NMR (400 MHz, CDCl$_3$) δ 8.09-8.02 (d, J=7.8 Hz, 2H), 7.99-7.94 (d, J=8.5 Hz, 1H), 7.87 (s, 1H), 7.58-7.52 (t, J=7.2 Hz, 1H), 7.49-7.40 (m, 3H), 7.22-7.13 (d, J=3.1 Hz, 2H), 4.49 (s, 2H), 2.63 (s, 6H). $^{13}$C NMR (100 MHz, CDCl$_3$) δ 197.86, 136.63, 133.23, 132.87, 132.29, 132.04, 131.61, 131.56, 128.69, 127.03, 126.63, 126.15, 125.20, 125.13, 45.02, 19.44, 19.38; HRMS calcd for $C_{20}H_{18}O$ $[M+1]^+$: 274.1358. Found: 274.1357.

2-(6,7-dimethylnaphthalen-2-yl)-1-phenylethanone (3da)

Light yellow solid, 91% yield, m.p. 142-144° C. $^1H$ NMR (400 MHz, $CDCl_3$) δ 8.07-7.98 (d, J=7.8 Hz, 2H), 7.71-7.65 (d, J=8.3 Hz, 1H), 7.59 (s, 1H), 7.56-7.50 (d, J=10.1 Hz, 3H), 7.46-7.39 (t, J=7.8 Hz, 2H), 7.31-7.26 (m, 1H), 4.40 (s, 2H), 2.39 (s, 6H). $^{13}C$ NMR (100 MHz, $CDCl_3$) δ 197.96, 136.59, 135.88, 135.48, 133.17, 132.50, 131.28, 131.16, 128.74, 128.66, 127.37, 127.15, 127.14, 127.09, 126.66, 45.88, 20.27, 20.23; HRMS calcd for $C_{20}H_{18}O$ $[M+1]^+$: 274.1358. Found: 274.1357.

2-(6,7-dibromonaphthalen-2-yl)-1-phenylethanone (3ea)

Yellow solid, 89% yield, m.p. 152-154° C. $^1H$ NMR (400 MHz, $CDCl_3$) δ 8.11 (s, 1H), 8.08 (s, 1H) 8.07-8.00 (m, 2H), 7.72-7.69 (d, J=8.6 Hz, 1H), 7.61-7.56 (m, 2H), 7.51-7.46 (t, J=7.6 Hz, 2H), 7.45-7.56 (m, 1H) 4.44 (s, 2H). $^{13}C$ NMR (100 MHz, $CDCl_3$) δ 197.06, 136.46, 133.79, 133.43, 133.18, 132.01, 131.96, 129.12, 128.77, 128.56, 127.22, 127.10, 122.27, 121.81, 45.45, 29.70; HRMS calcd for $C_{18}H_{12}Br_2O$ $[M+1]^+$ 401.9255. Found: 401.9247.

7-(phenylethynyl)-2,3-dihydronaphtho [2,3-b][1,4] dioxine (3ga)

Light yellow solid, 90% yield, m.p. 130-132° C. $^1H$ NMR (400 MHz, $CDCl_3$) δ 7.87 (s, 1H), 7.63-7.59 (d, J=8.6 Hz, 1H), 7.58-7.53 (m, 2H), 7.42-7.39 (m, 1H), 7.38-7.33 (m, 3H), 7.24 (s, 2H), 4.36 (s, 4H). $^{13}C$ NMR (100 MHz, $CDCl_3$) δ 144.68, 144.48, 131.60, 130.01, 129.11, 129.03, 128.35, 128.12, 126.86, 126.50, 123.50, 118.74, 112.64, 112.52, 90.14, 89.14, 64.49, 64.43; HRMS calcd for $C_{20}H_{14}O_2$ $[M+1]^+$: 286.0994. Found: 286.1001.

6-(phenylethynyl) naphtho [2,3-d][1,3] dioxole (3ha)

Light yellow solid, 77% yield, m.p. 154-155° C. $^1H$ NMR (400 MHz, $CDCl_3$) δ 7.87 (s, 1H), 7.64-7.61 (d, J=8.5 Hz, 1H), 7.58-7.55 (m, 2H), 7.46-7.43 (m, 1H), 7.39-7.34 (m, 3H), 7.11-7.08 (d, J=3.7 Hz, 2H), 6.05 (s, 2H). $^{13}C$ NMR (100 MHz, $CDCl_3$) δ 148.30, 148.13, 131.60, 130.45, 130.18, 130.16, 128.36, 128.16, 127.16, 127.04, 123.46, 119.02, 103.93, 103.71, 101.22, 89.91, 89.24; HRMS calcd for $C_{19}H_{12}O_2$ $[M+1]^+$: 272.0837. Found: 272.0848.

Cytotoxicity Assay

In this study, all compounds were dissolved in dimethyl sulfoxide (DMSO) to make stock solutions and further diluted in culture medium for this experiment. Human cancer cell lines, including one gastric adenocarcinoma cell line (MKN-45), one colon carcinoma cell line (DLD-1), one esophageal carcinoma cell line (KYSE-150) and one hepatocellular carcinoma cell line (HepG2) were cultured in RPMI 1640 or DMEM medium, containing 10% fetal bovine serum and 1% antibiotics (Penicillin and strep). The cell lines were cultured at 37° C. in a humidified environment containing 5% $CO_2$. To determine the effects of the compounds on cell viability, a standard colorimetric 3-(4,5-dimethylthiazol-2-yl)-2,5-diphenyltetrazolium bromide (MTT) assay was used to test the cell number. Cells were seeded in a 96-well plate ($4\times10^3$ cells/well) and allowed to attach overnight. After the recovery, cells were treated with 1.56, 3.125, 6.25, 12.5, 25, 50 µM of compounds in culture medium for 48 hrs. Then, 20 µL of MTT (5 mg/mL stock in PBS) per well was added into the medium (200 µL) and incubated for 4 hrs at 37° C. Finally, the culture medium was removed and 200 µL of DMSO were added to dissolve the purple formazan crystals. Absorbance of the solution was measured using microplate reader spectrophotometer (Bio-Rad Laboratories, Inc., Hercules, Calif.) at a wavelength of 570 nm.

Wound Healing Assay

A wound-healing assay was performed as follows: cells were seeded in 12 wells plate at 50% confluence in completed medium. After 24 hrs seeding, the monolayer was wounded by scoring with a sterile plastic tip (1 mL), then washed several times with medium to remove cell debris and then incubated in conditioned medium in the absence or presence of tested compounds for various periods of time up to 48 h. The concentration did not alter the viability of KYSE-150 cells were chosen. Cell migration into the wound surface was monitored by Olympus IX71 microscopy and digitally photographed.

In accordance with a first aspect of the present invention, there is provided anti-tumor or anti-cancer compounds for treating cancer synthesized via steps comprising adding a Pd complex, a ligand and a first solvent in a first noble gas atmosphere to form a first mixture;

stirring the first mixture at a first given temperature for a first given time duration;

adding $CF_3SO_3Ag$ to the stirred first mixture to form a second mixture;

stirring the second mixture for a second given time duration;

adding an oxobenzonorbornadienes derivative and a second solvent to the stirred second mixture to form a third mixture;

stirring the third mixture for a third given time duration;

adding a terminal alkynes to the third mixture to form a fourth mixture;

stirring the fourth mixture in a second noble gas atmosphere at a second given temperature until the complete consumption of the oxobenzonorbornadienes derivative;

evaporating the solvents in the stirred fourth mixture to obtain residue; and purifying the residue to obtain the anti-tumor or anti-cancer compounds.

In a first embodiment of the first aspect of the present invention there is provided anti-tumor or anti-cancer compounds, being of a structure of formula (I) or formula (II):

(II)

wherein each of $R_1$, $R_2$, $R_3$, $R_4$ is selected from a group consisting of H, OH, $OCH_2CH_2O$, $OCH_2O$, $OCF_3$, $CF_3$, $CH_2CH_2OH$, aryl, aryloxyl, halogen, alkyl, alkenyl, alkynyl, hydroxyl, alkoxyl, amine and nitro groups, and wherein each of $R_5$, $R_6$, $R_7$, $R_8$, $R_9$ is selected from a group consisting of H, OH, $OCH_2CH_2O$, $OCH_2O$, $OCF_3$, $CF_3$, $CH_2CH_2OH$, aryl, aryloxyl, halogen, alkyl, alkenyl, alkynyl, hydroxyl, alkoxyl, amine, nitro, nitrile, alkylthio, alkyl sulfonyl, and aryl sulfonyl groups.

In a second embodiment of the first aspect of the present invention there is provided anti-tumor or anti-cancer compounds comprising 2-(naphthalen-2-yl)-1-phenylethanone;
1-(4-methoxyphenyl)-2-(naphthalen-2-yl) ethanone;
1-(2-methoxyphenyl)-2-(naphthalen-2-yl) ethanone;
1-(3-methoxyphenyl)-2-(naphthalen-2-yl) ethanone;
1-(3,5-dimethoxyphenyl)-2-(naphthalen-2-yl) ethanone;
1-(4-fluorophenyl)-2-(naphthalen-2-yl) ethanone;
2-(naphthalen-2-yl)-1-(4-(trifluoromethoxy) phenyl) ethanone;
1-(4-bromophenyl)-2-(naphthalen-2-yl) ethanone;
2-(naphthalen-2-yl)-1-(p-tolyl) ethanone;
2-(naphthalen-2-yl)-1-(4-phenoxyphenyl) ethanone;
1-(4-(hydroxymethyl)phenyl)-2-(naphthalen-2-yl) ethanone;
2-(naphthalen-2-yl)-1-(4-(trifluoromethyl) phenyl) ethanone;
4-(2-(naphthalen-2-yl) acetyl) benzonitrile;
2-(naphthalen-2-yl)-1-phenylethanone-2-D;
2-(5,8-dimethoxynaphthalen-2-yl)-1-phenylethanone;
2-(5,8-dimethylnaphthalen-2-yl)-1-phenylethanone;
2-(6,7-dimethylnaphthalen-2-yl)-1-phenylethanone;
2-(6,7-dibromonaphthalen-2-yl)-1-phenylethanone;
7-(phenylethynyl)-2,3-dihydronaphtho [2,3-b][1,4] dioxine; and
6-(phenylethynyl) naphtho [2,3-d][1,3] dioxole.

In a third embodiment of the first aspect of the present invention there is provided anti-tumor or anti-cancer compounds are of a structure of the chemical formula 3aa, 3ab, 3ac, 3ad, 3ae, 3af, 3ag, 3ah, 3ai, 3aj, 3ak, 3al, 3am, 3an, 3ba, 3ca, 3da, 3ea, 3ga, and 3ha:

3aa

3ab

3ac

3ad

3ae

3af

3ag

3ah

3ai

In a fourth embodiment of the first aspect of the present invention there is provided anti-tumor or anti-cancer compounds wherein the Pd complex comprises $Pd(OAc)_2$, $C_{10}H_{14}O_4Pd$, $PdBr_2$, $Pd(CF_3COO)_2$, $Pd(C_6HF_6O_2)_2$, $PdCl_2$, $PdI_2$, and $C_6H_{10}Pd_2Cl_2$.

In a fifth embodiment of the first aspect of the present invention there is provided anti-tumor or anti-cancer compounds wherein the ligand comprises (±)-Binap, Xantphos, DPEphos, Dppf, Dppb, and $PPh_3$.

In a sixth embodiment of the first aspect of the present invention there is provided anti-tumor or anti-cancer compounds wherein the first solvent comprises DCE, DCM, DME, THF, and Toluene.

In a seventh embodiment of the first aspect of the present invention there is provided anti-tumor or anti-cancer compounds wherein the second solvent comprises DCE, DCM, DME, THF, and Toluene.

In an eighth embodiment of the first aspect of the present invention there is provided anti-tumor or anti-cancer compounds wherein the first noble gas and/or second noble gas comprises argon gas.

In a ninth embodiment of the first aspect of the present invention there is provided anti-tumor or anti-cancer compounds wherein the first and/or second given temperature ranges between 34° C. to 76° C., and is preferably 55° C.

In a tenth embodiment of the first aspect of the present invention there is provided anti-tumor or anti-cancer compounds wherein the first and/or second given temperature is room temperature.

In an eleventh embodiment of the first aspect of the present invention there is provided anti-tumor or anti-cancer compounds wherein the first and/or second and/or third given time duration is at least 10 minutes.

In a twelfth embodiment of the first aspect of the present invention there is provided anti-tumor or anti-cancer compounds wherein the oxobenzonorbornadienes derivative is of a structure of formula (III):

(III)

wherein $R_1$ is selected from a group consisting of H, OMe, Me, $OCH_2CH_2O$, $OCH_2O$, Ph, and OPh; $R_2$ is selected form a group consisting of H, Me, Br, Cl, F, $OCH_2$, OMe, $OCH_2CH_2O$, $OCH_2O$, Ph, and OPh; $R_3$ is selected from a group consisting of H, Me, Br, Cl, F, $CH_2O$, O, OMe, $OCH_2CH_2O$, $OCH_2O$, Ph, and OPh; and $R_4$ is selected from a group consisting of H, OMe, Me, $OCH_2CH_2O$, $OCH_2O$, Ph, and OPh.

In a thirteenth embodiment of the first aspect of the present invention there is provided anti-tumor or anti-cancer compounds wherein the terminal alkynes is of a structure of formula (IV):

(IV)

wherein $R_1$ is selected from a group consisting of H and D; and $R_2$ is selected from a group consisting of Ph, 4-$MeOC_6H_4$, 2-$MeOC_6H_4$, 3-$MeOC_6H_4$, 3,5-$diMeOC_6H_3$, 4-$FC_6H_4$, 4-$PhOC_6H_4$, 4-$CF_3OC_6H_4$, 4-$BrC_6H_4$, 4-$MeC_6H_4$, 4-$OHCH_2C_6H_4$, 4-$CF_3C_6H_4$, and 4-$CNC_6H_4$.

In a fourteenth embodiment of the first aspect of the present invention there is provided anti-tumor or anti-cancer compounds wherein the evaporation method comprises vacuum evaporation.

In a fifteenth embodiment of the first aspect of the present invention there is provided anti-tumor or anti-cancer compounds wherein the purification method comprises silica gel column chromatography.

In a sixteenth embodiment of the first aspect of the present invention there is provided anti-tumor or anti-cancer compounds wherein the cancer treated comprises gastric cancer, colon cancer, esophageal cancer and liver cancer.

In a second aspect of the present invention there is provided anti-tumor or anti-cancer compounds comprising phenylacetophenone derivatives based compounds.

In a first embodiment of the second aspect of the present invention there is provided anti-tumor or anti-cancer compounds comprising 2-(naphthalen-2-yl)-1-phenylethanone;
1-(4-methoxyphenyl)-2-(naphthalen-2-yl) ethanone;
1-(2-methoxyphenyl)-2-(naphthalen-2-yl) ethanone;
1-(3-methoxyphenyl)-2-(naphthalen-2-yl) ethanone;
1-(3,5-dimethoxyphenyl)-2-(naphthalen-2-yl) ethanone;
1-(4-fluorophenyl)-2-(naphthalen-2-yl) ethanone;
2-(naphthalen-2-yl)-1-(4-(trifluoromethoxy) phenyl) ethanone;
1-(4-bromophenyl)-2-(naphthalen-2-yl) ethanone;
2-(naphthalen-2-yl)-1-(p-tolyl) ethanone;
2-(naphthalen-2-yl)-1-(4-phenoxyphenyl) ethanone;
1-(4-(hydroxymethyl)phenyl)-2-(naphthalen-2-yl) ethanone;
2-(naphthalen-2-yl)-1-(4-(trifluoromethyl) phenyl) ethanone;
4-(2-(naphthalen-2-yl) acetyl) benzonitrile;
2-(naphthalen-2-yl)-1-phenylethanone-2-D;
2-(5,8-dimethoxynaphthalen-2-yl)-1-phenylethanone;
2-(5,8-dimethylnaphthalen-2-yl)-1-phenylethanone;
2-(6,7-dimethylnaphthalen-2-yl)-1-phenylethanone;
2-(6,7-dibromonaphthalen-2-yl)-1-phenylethanone;
7-(phenylethynyl)-2,3-dihydronaphtho [2,3-b][1,4] dioxine; and
6-(phenylethynyl) naphtho [2,3-d][1,3] dioxole.

In a second embodiment of the second aspect of the present invention there is provided anti-tumor or anti-cancer compounds, being of a structure of the chemical formula 3aa, 3ab, 3ac, 3ad, 3ae, 3af, 3ag, 3ah, 3ai, 3aj, 3ak, 3al, 3am, 3an, 3ba, 3ca, 3da, 3ea, 3ga, and 3ha:

3aa

3ab

3ac

3ad

3ae

3af

3ag

In a third embodiment of the second aspect of the present invention there is provided anti-tumor or anti-cancer compounds wherein the cancer treated comprises gastric cancer, colon cancer, esophageal cancer and liver cancer.

INDUSTRIAL APPLICABILITY

This invention relates to the quick and efficient synthesis of anti-tumor or anti-cancer compounds. More particularly, it relates to the quick and efficient synthesis of anti-tumor or anti-cancer compounds comprising phenylacetophenone derivatives using oxabenzonorbornadienes with terminal alkynes.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in

What we claim:

1. A method of synthesizing a compound having a structure of formula (I) or formula (II):

wherein each of $R_1$, $R_2$, $R_3$, $R_4$ is selected from a group consisting of H, OH, $OCH_2CH_2O$, $OCH_2O$, $OCF_3$, $CF_3$, $CH_2CH_2OH$, aryl, aryloxyl, halogen, alkyl, alkenyl, alkynyl, hydroxyl, alkoxyl, amine and nitro groups, among them one of $OCH_2CH_2O$ and $OCH_2O$ is substituted between $R_1$ and $R_2$, or $R_2$ and $R_3$, or $R_3$ and $R_4$, and wherein each of $R_5$, $R_6$, $R_7$, $R_8$, $R_9$ is selected from a group consisting of H, OH, $OCH_2CH_2O$, $OCH_2O$, $OCF_3$, $CF_3$, $CH_2CH_2OH$, aryl, aryloxyl, halogen, alkyl, alkenyl, alkynyl, hydroxyl, alkoxyl, amine, nitro, nitrile, alkylthio, alkyl sulfonyl, and aryl sulfonyl groups, among them one of $OCH_2CH_2O$ and $OCH_2O$ is substituted between $R_1$ and $R_2$, or $R_2$ and $R_3$, or $R_3$ and $R_4$, comprising steps of:
adding a Pd complex, a ligand and a first solvent in a first noble gas atmosphere to form a first mixture;
stirring the first mixture at a first given temperature for a first given time duration;
adding $CF_3SO_3Ag$ to the stirred first mixture to form a second mixture;
stirring the second mixture for a second given time duration;
adding an oxobenzonorbornadiene derivative and a second solvent to the stirred second mixture to form a third mixture;
stirring the third mixture for a third given time duration;
adding a terminal alkyne to the third mixture to form a fourth mixture;
stirring the fourth mixture in a second noble gas atmosphere at a second given temperature until the complete consumption of the oxobenzonorbornadiene derivative;
evaporating the solvents in the stirred fourth mixture to obtain residue; and
purifying the residue to obtain the compound;

wherein the oxobenzonorbornadiene derivative is of a structure of formula (III):

wherein $R_1$ is selected from a group consisting of H, OMe, Me, $OCH_2CH_2O$, $OCH_2O$, Ph, and OPh; $R_2$ is selected from a group consisting of H, Me, Br, Cl, F, $OCH_2$, OMe, $OCH_2CH_2O$, $OCH_2O$, Ph, and OPh; $R_3$ is selected from a group consisting of H, Me, Br, Cl, F, $CH_2O$, O, OMe, $OCH_2CH_2O$, $OCH_2O$, Ph, and OPh; and $R_4$ is selected from a group consisting of H, OMe, Me, $OCH_2CH_2O$, $OCH_2O$, Ph, and OPh; and wherein the terminal alkyne is of a structure of formula (IV):

$$R_1\text{—}\!\!=\!\!\text{—}R_2 \qquad (IV),$$

wherein $R_1$ is selected from a group consisting of H and D; and $R_2$ is selected from a group consisting of Ph, 3-$MeOC_6H_4$, 3,5-$diMeOC_6H_3$, 4-$FC_6H_4$, 4-$PhOC_6H_4$, 4-$CF_3OC_6H_4$, 4-$BrC_6H_4$, 4-$MeC_6H_4$, 4-$OHCH_2C_6H_4$, 4-$CF_3C_6H_4$, and 4-$CNC_6H_4$.

2. The method of claim 1, wherein said compound comprises:
1-(3,5-dimethoxyphenyl)-2-(naphthalen-2-yl) ethanone;
1-(4-fluorophenyl)-2-(naphthalen-2-yl) ethanone;
2-(naphthalen-2-yl)-1-(4-(trifluoromethoxy) phenyl) ethanone;
1-(4-bromophenyl)-2-(naphthalen-2-yl) ethanone;
2-(naphthalen-2-yl)-1-(4-phenoxyphenyl) ethanone;
2-(naphthalen-2-yl)-1-(4-(trifluoromethyl) phenyl) ethanone;
4-(2-(naphthalen-2-yl) acetyl) benzonitrile;
2-(naphthalen-2-yl)-1-phenylethanone-2-D;
2-(5,8-dimethoxynaphthalen-2-yl)-1-phenylethanone;
2-(5,8-dimethylnaphthalen-2-yl)-1-phenylethanone;
2-(6,7-dimethylnaphthalen-2-yl)-1-phenylethanone;
2-(6,7-dibromonaphthalen-2-yl)-1-phenylethanone;
7-(phenylethynyl)-2,3-dihydronaphtho [2,3-b][1,4] dioxine; and
6-(phenylethynyl) naphtho [2,3-d][1,3] dioxole.

3. The method according to claim 1 wherein the Pd complex comprises $Pd(OAc)_2$, $C_{10}H_{14}O_4Pd$, $PdBr_2$, $Pd(CF_3COO)_2$, $Pd(C_6HF_6O_2)_2$, $PdCl_2$; $PdI_2$; and $C_6H_{10}Pd_2Cl_2$.

4. The method according to claim 1 wherein the ligand comprises (±)-Binap, Xantphos, DPEphos, Dppf, Dppb, and $PPh_3$.

5. The method according to claim 1 wherein the first solvent comprises 1,2-dichloroethane, dichloromethane, dimethoxyethane, tetraphdrofuran and toluene.

6. The method according to claim 1 wherein the second solvent comprises 1,2-dichloroethane, dichloromethane, dimethoxyethane, tetraphdrofuran and toluene.

7. The method according to claim 1 wherein the first noble gas and/or second noble gas comprises argon gas.

8. The method according to claim 1 wherein the first and/or second given temperature ranges between 34° C. to 76° C.

9. The method according to claim 1 wherein the first and/or second given temperature is room temperature.

10. The method according to claim 1 wherein the first and/or second and/or third given time duration is at least 10 minutes.

11. The method according to claim 1 wherein the evaporation method comprises vacuum evaporation.

12. The method according to claim 1 wherein the purification method comprises silica gel column chromatography.

13. A method of treating esophageal carcinoma in a subject by administering a compound having a structure of formula (I) or formula (II) to the subject, wherein each of $R_1$, $R_2$, $R_3$, $R_4$ is selected from a group consisting of H, OH, $OCH_2CH_2O$, $OCH_2O$, $OCF_3$, $CF_3$, $CH_2CH_2OH$, aryl, aryloxyl, halogen, alkyl, alkenyl, alkynyl, hydroxyl, alkoxyl, amine and nitro groups, among them one of $OCH_2CH_2O$ and $OCH_2O$ is substituted between $R_1$ and $R_2$, or $R_2$ and $R_3$, or $R_3$ and $R_4$; and wherein each of $R_5$, $R_6$, $R_7$, $R_8$, $R_9$ is selected from a group consisting of H, OH, $OCH_2CH_2O$, $OCH_2O$, $OCF_3$, $CF_3$, $CH_2CH_2OH$, aryl, aryloxyl, halogen, alkyl, alkenyl, alkynyl, hydroxyl, alkoxyl, amine, nitro, nitrile, alkylthio, alkyl sulfonyl, and aryl sulfonyl groups, among them one of $OCH_2CH_2O$ and $OCH_2O$ is substituted between $R_1$ and $R_2$, or $R_2$ and $R_3$, or $R_3$ and $R_4$.

14. The method according to claim 13, wherein the compound is selected from a group consisting of: 2-(naphthalen-2-yl)-1-phenylethanone, 1-(4-methoxyphenyl)-2-(naphthalen-2-yl) ethanone, 1-(2-methoxyphenyl)-2-(naphthalen-2-yl) ethanone, 1-(3-methoxyphenyl)-2-(naphthalen-2-yl) ethanone, 1-(3,5-dimethoxyphenyl)-2-(naphthalen-2-yl) ethanone, 1-(4-fluorophenyl)-2-(naphthalen-2-yl) ethanone, 2-(naphthalen-2-yl)-1-(4-(trifluoromethoxy) phenyl) ethanone, 1-(4-bromophenyl)-2-(naphthalen-2-yl) ethanone, 2-(naphthalen-2-yl)-1-(p-tolyl) ethanone, 2-(naphthalen-2-yl)-1-(4-phenoxyphenyl) ethanone, 1-(4-(hydroxymethyl)phenyl)-2-(naphthalen-2-yl) ethanone, 2-(naphthalen-2-yl)-1-(4-(trifluoromethyl) phenyl) ethanone, 4-(2-(naphthalen-2-yl) acetyl) benzonitrile, 2-(naphthalen-2-yl)-1-phenylethanone-2-D, 2-(5,8-dimethoxynaphthalen-2-yl)-1-phenylethanone, 2-(5,8-dimethylnaphthalen-2-yl)-1-phenylethanone, 2-(6,7-dimethylnaphthalen-2-yl)-1-phenylethanone, 2-(6,7-dibromonaphthalen-2-yl)-1-phenylethanone, 7-(phenylethynyl)-2,3-dihydronaphtho [2,3-b][1,4] dioxine, and 6-(phenylethynyl) naphtho [2,3-d][1,3] dioxole.

* * * * *